United States Patent
Sugimoto et al.

(10) Patent No.: US 9,655,852 B2
(45) Date of Patent: May 23, 2017

(54) TABLETS CONTAINING A 1-(β-D-GLUCOPYRANOSYL)-3-(PHENYLTHIENYLMETHYL)BENZENE COMPOUND

(71) Applicant: MITSUBISHI TANABE PHARMA CORPORATION, Osaka-shi, Osaka (JP)

(72) Inventors: Masaaki Sugimoto, Osaka (JP); Hajime Kinoshita, Osaka (JP); Takayuki Tokuda, Osaka (JP)

(73) Assignee: MITSUBISHI TANABE PHARMA CORPORATION, Osaka-Shi (JP)

( * ) Notice: Subject to any disclaimer, the term of this patent is extended or adjusted under 35 U.S.C. 154(b) by 0 days.

(21) Appl. No.: 15/133,889

(22) Filed: Apr. 20, 2016

(65) Prior Publication Data

US 2016/0228375 A1 Aug. 11, 2016

Related U.S. Application Data

(63) Continuation of application No. 13/697,225, filed as application No. PCT/JP2011/061354 on May 11, 2011, now abandoned.

(60) Provisional application No. 61/333,312, filed on May 11, 2010.

(51) Int. Cl.
  *A61K 9/20* (2006.01)
  *A61K 9/28* (2006.01)
  *A61K 31/7042* (2006.01)
  *A61K 31/7034* (2006.01)

(52) U.S. Cl.
  CPC .......... *A61K 9/2013* (2013.01); *A61K 9/2009* (2013.01); *A61K 9/2018* (2013.01); *A61K 9/2054* (2013.01); *A61K 9/284* (2013.01); *A61K 31/7034* (2013.01); *A61K 31/7042* (2013.01)

(58) Field of Classification Search
  None
  See application file for complete search history.

(56) References Cited

U.S. PATENT DOCUMENTS 6,635,278 B1   10/2003   Dahl et al.
2004/0033258 A1   2/2004   Koike

FOREIGN PATENT DOCUMENTS

WO   WO 2005/012326 A1   2/2005
WO   WO 2008/116179 A1   9/2008
WO   WO 2009/022010 A1   2/2009
WO   WO 2010/092125 A1   8/2010

OTHER PUBLICATIONS

"Additives and Processing Technology for Tablet and Capsule," Foods and Development, 2007, vol. 42, No. 12, pp. 37-42.
International Preliminary Report on Patentability and Written Opinion of the International Searching Authority for Application No. PCT/JP2011/061354 dated Nov. 22, 2012 (Forms PCT/IB/326, PCT/IB/373, and PCT/ISA/237).
International Search Report for PCT/JP2011/061354 mailed on Jul. 28, 2011.
Japan Office Action for Appl. No. 2012-551398 dated Dec. 6, 2013 (w/ English translation).
Shimada, Y. et al, "Formulation Technology, Formulation and Granule Design, Measurement of granular physical Properties in formulation," Pharm Tech Jpn, 2008, vol. 24, No. 10, pp. 2289-2298.
Written Opinion of the International Searching Authority for PCT/JP2011/061354 mailed on Jul. 28, 2011.

*Primary Examiner* — Robert A Wax
*Assistant Examiner* — Randeep Singh
(74) *Attorney, Agent, or Firm* — Birch, Stewart, Kolasch & Birch, LLP

(57) ABSTRACT

The present invention is directed to a tablet containing a 1-(β-D-glucopyranosyl)-3-(phenylthienylmethyl)benzene compound in high drug loading, in particular, containing the compound ranging from 30 to 95% by weight of tablet and pharmaceutically acceptable additives.

13 Claims, No Drawings

TABLETS CONTAINING A 1-(β-D-GLUCOPYRANOSYL)-3-(PHENYLTHIENYLMETHYL)BENZENE COMPOUND

CROSS-REFERENCE TO RELATED APPLICATIONS

This application is a Continuation of copending application Ser. No. 13/697,225, filed on Nov. 9, 2012, which was filed as PCT International Application No. PCT/JP2011/061354 on May 11, 2011, which claims the benefit under 35 U.S.C. §119(e) to U.S. Provisional Application No. 61/333,312, filed on May 11, 2010, all of which are hereby expressly incorporated by reference into the present application.

FIELD OF THE INVENTION

The present invention relates to a tablet containing a 1-(β-D-glucopyranosyl)-3-(phenylthienylmethyl)benzene derivative or a pharmaceutically acceptable salt thereof that can be used in the treatment of diabetes mellitus, obesity, diabetic complications, and the related diseases.

BACKGROUND OF THE INVENTION

WO 2005/012326 pamphlet discloses a class of compounds that are inhibitors of sodium-dependent glucose transporter (SGLT) and thus of therapeutic use for treatment of diabetes, obesity, diabetic complications, and the like. WO 2005/012326 pamphlet describes 1-(β-D-glucopyranosyl)-4-methyl-3-[5-(4-fluorophenyl)-2-thienylmethyl]benzene having the following formula:

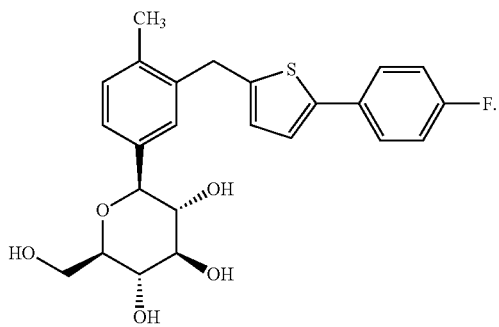

(A)

Compound (A) hemihydrate and a certain crystal form thereof are disclosed in International Patent Application WO 2008/069327. The disclosure of WO 2005/012326 and WO 2008/069327 is incorporated herein by reference in its entirety.

BRIEF DESCRIPTION OF THE INVENTION

The present invention relates to a tablet with high drug loading including a 1-(β-D-glucopyranosyl)-3-(phenylthienylmethyl)benzene derivative represented by formula (A):

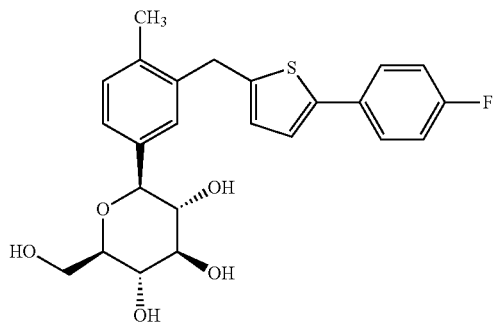

(A)

or a pharmaceutically acceptable salt thereof, as an active ingredient.

DETAILED DESCRIPTION OF THE INVENTION

The pharmaceutically acceptable salts of compound (A) include, for example, a salt with an inorganic acid such as hydrochloric acid, hydrobromic acid, hydroiodic acid, sulfuric acid, nitric acid, phosphoric acid, etc.; or a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid, etc.; or a salt with an acidic amino acid such as aspartic acid, glutamic acid, etc.

In addition, pharmaceutically acceptable salts of the compound of formula (A) include an intramolecular salt, hydrate, solvate or polymorphism thereof. Preferably, a pharmaceutically acceptable salt of compound (A) is hemihydrate.

Compound (A) is also known as canagliflozin.

The active pharmaceutical ingredient, i.e., compound (A) or a pharmaceutically acceptable salt thereof, possesses activity as an inhibitor of the sodium dependent glucose transporters found in the intestine and kidney, and therefore the tablet of the present invention can be used in the treatment or prevention of patients, such as human patients, for diseases or disorders associated with SGLT activity. Thus, the tablet of the present invention can be used for the treatment, prevention or delaying the progression or onset of diabetes mellitus (such as type 1 and type 2 diabetes mellitus), diabetic complications (such as diabetic retinopathy, diabetic neuropathy, diabetic nephropathy), delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, atherosclerosis, or hypertension.

In one embodiment, the invention relates to a tablet in the treatment or delaying the progression or onset of type II diabetes mellitus or obesity.

In another embodiment, the invention relates to a method for treating or delaying the progression or onset of diseases associated with SGLT activity comprising administering to a patient in need of such treatment a therapeutically effective amount of the tablet of the invention.

In another embodiment, the invention relates to a method for treating or delaying the progression or onset of type II diabetes mellitus or obesity comprising administering to a patient in need of such treatment a therapeutically effective amount of the tablet of the invention.

The tablet of the present invention may contain additives generally used in pharmaceutical solid tablets. Examples of the additives include bulking agents (or fillers), disintegrants, binders, lubricants, coating agents, surfactants, flavors, colorants and sweetenings.

Examples of the bulking agents or fillers suitable for use herein include lactose, sucrose, mannitol, xylitol, erythritol, sorbitol, maltitol, calcium citrate, calcium phosphate, and calcium aluminometasilicate. Examples of the bulking agents or fillers also include cellulose derivatives, such as microcrystalline cellulose or wood cellulose, lactose, sucrose, starch, pregelatinized starch, dextrose, mannitol, fructose, xylitol, sorbitol, corn starch, modified corn starch, inorganic salts such as calcium carbonate, calcium phosphate, dicalcium phosphate, calcium sulfate, dextrin/dextrates, maltodextrin, and compressible sugars. And mixtures of two or more above bulking agents or fillers can be used also. Mannitol is particularly suitable for use in the tablet of the present invention.

Examples of disintegrants suitable for use herein include croscarmellose sodium, crospovidone, starch, potato starch, pregelatinized starch, corn starch, sodium starch glycolate, microcrystalline cellulose, low substituted hydroxypropyl cellulose and other known disintegrants. Preferably, the disintegrant suitable for use in the tablet is croscarmellose sodium.

Examples of binders suitable for use herein include hydroxypropyl cellulose, corn starch, dextrin, pregelatinized starch, modified corn starch, polyvinyl pyrrolidone, hydroxypropyl methylcellulose, lactose, gum acacia, ethyl cellulose, cellulose acetate, polyethyleneglycol, as well as other conventional binding agents and/or mixtures of two or more thereof. Preferably, the binder suitable for use herein is hydroxypropyl cellulose.

Examples of lubricants suitable for use herein include magnesium stearate, zinc stearate, calcium stearate, talc, carnauba wax, stearic acid, palmitic acid, sodium stearyl fumarate, sodium laurel sulfate, glyceryl palrnitostearate, palmitic acid, myristic acid and hydrogenated vegetable oils and fats. In a preferable embodiment, the lubricant suitable for use herein is talc and/or sodium stearyl fumarate.

Examples of surfactants suitable for use herein include phospholipid, glycerin fatty acid ester, sorbitan fatty acid ester, polyoxyethylene fatty acid ester, polyethylene glycol fatty acid ester, polyoxyethylene hydrogenated castor oil, polyoxyethylene alkyl ether, and sucrose fatty acid ester.

Examples of flavors suitable for use herein include orange oil, fennel oil, cinnamon oil, clove oil, turpentine oil, peppermint oil, and eucalyptus oil.

Examples of colorants suitable for use herein include carotinoids, iron oxides and chlorophylls. Examples of colorants also include Food Color Red Nos. 2 and 3, Food Color Yellow Nos. 4 and 5, Food Color Green No. 3, Food Color Blue Nos. 1 and 2, aluminum lakes of these Food Colors, iron sesquioxide, and yellow iron sesquioxide.

Examples of sweetenings suitable for use herein include saccharine, and aspartame.

According to the present invention, the tablet comprises a) compound (A) or a pharmaceutically acceptable salt thereof and b) one or more pharmaceutically acceptable additives. Preferably, the active ingredient (i.e., compound (A) or a pharmaceutically acceptable salt thereof) is in an amount within the range of from about 30% to about 95% by weight of tablet. More preferably, the active ingredient is in an amount within the range of from about 50% to about 90% by weight of tablet. Preferably, the additives comprise a bulking agent (or a filler), a binder, a disintegrant, a lubricant, and optionally a coating agent.

In another embodiment of the present invention, the tablet comprises a) compound (A) or a pharmaceutically acceptable salt thereof, wherein compound (A) or a pharmaceutically acceptable salt thereof is present in an amount within the range of from 30 to 95% by weight of tablet; b) bulking agent (or filler) wherein the bulking agent or the filler is present in an amount within the range of from about 0 to 70% by weight of tablet; c) binder, wherein the binder is present in an amount within the range of from about 1 to 25% by weight of tablet; d) disintegrant, wherein the disintegrant is present in an amount within the range of from about 1 to 25% by weight of tablet; and e) lubricant, wherein the lubricant is present in an amount within the range of from about 0.25 to 20% by weight of tablet.

In a preferable embodiment, the tablet comprises (a) compound (A) or a pharmaceutically acceptable salt thereof and (b) talc and sodium stearyl fumarate. In this embodiment, the active ingredient (i.e., compound (A) or a pharmaceutically acceptable salt thereof) is preferably in an amount within the range of from about 30% to about 95% by weight of tablet. More preferably, the active ingredient is in an amount within the range of from about 50% to about 90% by weight of tablet. The tablet may further comprises additional pharmaceutically acceptable additives such as a bulking agent, a binder, a disintegrant, and optionally a coating agent.

In another preferable embodiment of the present invention, the tablet comprises a) compound (A) or a pharmaceutically acceptable salt thereof, wherein compound (A) or a pharmaceutically acceptable salt thereof is present in an amount within the range of from 50 to 90% by weight of tablet; b) bulking agent (or filler), wherein the bulking agent or the filler is present in an amount within the range of from about 5 to 15% by weight of tablet; c) binder, wherein the binder is present in an amount within the range of from about 1 to 5% by weight of tablet; d) disintegrant, wherein the disintegrant is present in an amount within the range of from about 1 to 5% by weight of tablet; and e) lubricant, wherein the lubricant is present in an amount within the range of from about 1 to 10% by weight of tablet.

In certain preferred embodiments of the present invention, the tablet comprises compound (A) or a pharmaceutically acceptable salt thereof in an amount greater than 65% by weight of the tablet. In certain further preferred embodiments of the present invention, the tablet comprises compound (A) or a pharmaceutically acceptable salt thereof in an amount within the range of 65% to 90% by weight of the tablet, preferably with the range of 65% to 75% by weight of the tablet.

In certain preferred embodiments of the present invention, the tablet comprises the bulking agent or the filler in an amount less than 25% by weight of the tablet. In certain further preferred embodiments of the present invention, the tablet comprises the bulking agent or filler in an amount within the range of 5% to 20% by weight of the tablet, preferably 10% to 15% by weight of the tablet.

In another preferable embodiment of the present invention, the tablet comprises a) compound (A) or a pharmaceutically acceptable salt thereof, wherein compound (A) or a pharmaceutically acceptable salt thereof is present in an amount of 70±2% by weight of tablet; b) bulking agent (or, wherein the bulking agent or the filler is present in an amount of 12±2% by weight of tablet; c) binder, wherein the binder is present in an amount of 3±1% by weight of tablet; d) disintegrant, wherein the disintegrant is present in an amount of 4±1% by weight of tablet; and e) lubricant, wherein the lubricant is present in an amount of 4±2% by weight of tablet.

Preferably, the bulking agent is D-mannitol, the binder is hydroxypropyl cellulose, the disintegrant is croscarmellose sodium, the lubricant is talc and sodium stearyl fumarate.

In a more preferable embodiment of the invention, the tablet further comprises a coating agent. The coating agent is present in an amount within the range of from about 0 to 25%, more preferably 0 to 15%, further more preferably 3 to 10% by weight of the tablet.

In a more preferable embodiment of the present invention, the tablet comprises a) compound (A) hemihydrate, wherein compound (A) hemihydrate is present in an amount of about 204 mg; b) D-mannitol, wherein D-mannitol is present in an amount of about 36 mg; c) hydroxypropyl cellulose, wherein hydroxypropyl cellulose is present in an amount of about 8 mg; d) croscarmellose sodium, wherein croscarmellose sodium is present in an amount of about 11.2 mg; e) talc, wherein talc is present in an amount of about 2.8 mg; and f) sodium stearyl fumarate, wherein sodium stearyl fumarate is present in an amount of about 8 mg.

In another more preferable embodiment of the present invention, the tablet comprises a) compound (A) hemihydrate, wherein compound (A) hemihydrate is present in an amount of about 102 mg; b) D-mannitol, wherein D-mannitol is present in an amount of about 18 mg; c) hydroxypropyl cellulose, wherein hydroxypropyl cellulose is present in an amount of about 4 mg; d) croscarmellose sodium, wherein croscarmellose sodium is present in an amount of about 5.6 mg; e) talc, wherein talc is present in an amount of about 1.4 mg; and f) sodium stearyl fumarate, wherein sodium stearyl fumarate is present in an amount of about 4 mg.

In another more preferable embodiment of the present invention, the tablet comprises a) compound (A) hemihydrate, wherein compound (A) hemihydrate is present in an amount of about 51 mg; b) D-mannitol, wherein D-mannitol is present in an amount of about 9 mg; c) hydroxypropyl cellulose, wherein hydroxypropyl cellulose is present in an amount of about 2 mg; d) croscarmellose sodium, wherein croscarmellose sodium is present in an amount of about 2.8 mg; e) talc, wherein talc is present in an amount of about 0.7 mg; and f) sodium stearyl fumarate, wherein sodium stearyl fumarate is present in an amount of about 2 mg.

It is a characteristic of the tablet of the present invention that it contains a high content of compound (A) or a pharmaceutically acceptable salt thereof given the relatively small amount of additives. This enables the production of physically small tablets. The tablets of the invention are, despite the high drug loading, small, and, therefore, convenient to administer. This leads to a better patient compliance.

Also, according to the present invention, due to the remarkable increase in compactibility of granules for tableting, the tableting troubles such as binding, capping and sticking can be minimized and the ejection forces can be decreased during the tableting processes. In addition, the tablets of the present invention have superior characteristics with respect to tablet hardness, friability and disintegration.

The total amount of additives in a given unit may be about 70% or less by weight of tablet, more particularly about 50% or less.

In another embodiment, the invention provides a tablet comprising from 25 mg to 600 mg of compound (A) or a pharmaceutically acceptable salt thereof, e.g., of from 50 mg to about 400 mg. Most preferably, the tablets according to the invention are tablets containing about 50 mg, tablets containing about 100 mg, tablets containing about 200 mg and/or tablets containing about 300 mg, of compound (A) or a pharmaceutically acceptable salt thereof.

The tablet of the present invention can be prepared by the process comprising (a) forming granules comprising the compound (A) or a pharmaceutically acceptable salt thereof together with pharmaceutically acceptable additives, (b) mixing the obtained granules together with pharmaceutically acceptable extra additives, (c) forming the tablet by compressing the mixture obtained in step (b), and optionally (d) coating the tablet.

The granules comprise compound (A) or a pharmaceutically acceptable salt thereof and one or more additives. Preferably, the granules comprise compound (A) or a pharmaceutically acceptable salt thereof and one or more binders and bulking agents (or fillers). The amount of one or more binders in the granule is ranging from about 1 to 25%, preferably 1 to 20% and more preferably 1 to 15% by weight of tablet. The amount of one or more bulking agents (or fillers) in the granule is ranging from about 0 to 70%, preferably 0 to 60% and more preferably 0 to 50% by weight of tablet. Preferable examples of the binders include hydroxypropyl cellulose. The amount of hydroxypropyl cellulose in the granule may vary from 1 to 15%, preferably 1 to 10% by weight of tablet. Preferable examples of the bulking agents (or fillers) include D-mannitol. The amount of D-mannitol in the granule may vary from about 0 to 70%, in particular 0 to 50% by weight of tablet.

Granules can be prepared by methods well known to those skilled in the art. Examples of such methods include wet granulation, dry granulation, layering granulation, melt-granulation, and impregnated-granulation.

For example, compound (A) or a pharmaceutically acceptable salt thereof and the pharmaceutically acceptable additives are mixed together and the mixture is processed for granulation with water and/or binder solution using a wet high-shear granulator to form the wet-granulates. The wet-granulates may be then, dried using a fluid bed dryer.

The tablets can be formed by mixing the granules with one or more extra additives (preferably, one or more disintegrants and one or more lubricants), and compressing the obtained mixture. The preferable example of the disintegrants is croscarmellose sodium. The amount of disintegrant as an extra additive is ranging from about 1 to 25%, more preferably 1 to 20% by weight of tablet. Preferable examples of lubricants include talc and sodium stearyl fumarate. Preferably, the amount of lubricants as an extra additive is ranging from about 0.25 to 20%, more preferably 0.25 to 15% by weight of tablet. Most preferably, the amount of talc is ranging from about 0.25 to 10%, more preferably, 0.25 to 5% by weight of tablet, and the amount of sodium stearyl fumarate is ranging from about 0.25 to 10%, more preferably, 0.25 to 5% by weight of tablet.

According to the invention, the tablets are formed by compressing the mixture of the granules and extra additives. The compression can be conducted using a conventional tableting machine such as rotary tableting machine, single punch tableting machine, and the like, with a compressing pressure of generally about from 1 to 30 KN.

Optionally, the tablets may be coated with the aim of, for example, preventing abrasion wear, masking bitterness, improving stability. The coating can be carried out in a conventional manner; however, it is preferable to confine the coating amount to such an extent that does not disturb the dissolution of compound (A) or a pharmaceutically acceptable salt thereof.

Preferably, the amount of the coating layer of the tablet, where present, is ranging from about 0% to about 25% by weight of tablet, more preferably, 0% to 15% by weight of tablet.

Suitable examples of polymer for the coating include hydroxypropyl methylcellulose, polyvinyl alcohol, ethyl cellulose, methacrylic polymers, hydroxypropyl cellulose, and starch. The coating layer can also optionally include an anti-adherent or glidant such as fumed silica, or magnesium stearate, for example. The coating layer can also optionally include an opacifying agent such as titanium dioxide, and a colorant such as iron oxide based colorant(s). Examples of commercially available coating agent include Opadry® HP and Opadry® II.

The tablet may vary in shape and be, for example, round, oval, or any other suitable shape. A characteristic of tablets according to the invention is their small size having regard to the amount of compound (A) or a pharmaceutically acceptable salt thereof.

In a preferred embodiment of the invention tablets obtained by the compression methods described above are round or oval. For example, the round tablet may be of the following dimensions, e.g., 3 to 14 mm in diameter, preferably 5 to 12 mm. The thickness of the tablet may be from 1.5 to 7 mm, preferably 2.5 to 6 mm.

The tablets of the invention may furthermore be colored. Colorants suitable for use herein include carotinoids, iron oxides or chlorophyll.

Preferably the tablet is chosen to exhibit immediate release of compound (A) or a pharmaceutically acceptable salt thereof, e.g., compound (A) hemihydrate.

Procedures which may be used may be conventional or known in the art or based on such procedures, e.g., those described in Remington's Pharmaceutical Sciences.

It will be understood that the dose of the tablet of the invention for any particular patient will depend upon a variety of factors including the age, the body weight, general health, drug combination with one or more active drugs, type and severity of the disease.

The tablet of the present invention can be optionally administered to a patient in need of treatments in combination with one or more other therapeutic agents such as other anti-diabetic agents, anti-hyper glycemic agents and/or agents for treatment of other diseases.

Examples of the other anti-diabetic agents and anti-hyper glycemic agents include insulin, insulin secretagogues, insulin sensitizers, or other antidiabetic agents having an action mechanism different from SGLT inhibition. Specifically, examples of these agents are biguanides, sulfonylureas, α-glucosidase inhibitors, PPARγ agonists (e.g., thiazolidinedione compounds), PPARα/γ dual agonists, PPARpan agonists, dipeptidyl peptidase IV (DPP4) inhibitors, mitiglinide, nateglinide, repaglinide, insulin, glucagon-like peptide-1 (GLP-1) and its receptor agonists, PTP1B inhibitors, glycogen phosphorylase inhibitors, RXR modulators, glucose 6-phosphatase inhibitors, GPR40 agonists/antagonists, GPR119 agonists, GPR120 agonists, glucokinase (GK) activators, and fructose 1,6-bisphosphatase (FBPase) inhibitors.

Examples of the agents for treatment of other diseases include anti-obesity agents, anti-hypertensive agents, anti-platelet agents, anti-atherosclerotic agents and hypolipidemic agents.

The anti-obesity agents which may be optionally employed in combination with the compound of the present invention include β3 adrenergic agonists, lipase inhibitors, serotonin (and dopamine) reuptake inhibitors, thyroid hormone receptor beta drugs, anorectic agents, NPY antagonists, Leptin analogs, MC4 agonists and CB1 antagonists.

The anti-platelet agents which may be optionally employed in combination with the compound of the present invention include abciximab, ticlopidine, eptifibatide, dipyridamole, aspirin, anagrelide, tirofiban and clopidogrel.

The anti-hypertensive agents which may be optionally employed in combination with the compound of the present invention include ACE inhibitors, calcium antagonists, alpha-blockers, diuretics, centrally acting agents, angiotensin-II antagonists, beta-blockers, renin inhibitors and vasopeptidase inhibitors.

The hypolipidemic agents which may be optionally employed in combination with the compound of the present invention include MTP inhibitors, HMG CoA reductase inhibitors, squalene synthetase inhibitors, squalene epoxidase inhibitors, fibric acid derivatives, ACAT inhibitors, lipoxygenase inhibitors, cholesterol absorption inhibitors, ileal Na+/bile acid cotransporter inhibitors, upregulators of LDL receptor activity, bile acid sequestrants, nicotinic acid and derivatives thereof, CETP inhibitors, and ABC A1 upregulators.

The dosage of those agents may vary according to ages, body weight, conditions of patients, administration routes, and dosage forms.

Where the tablet of the present invention is used in combination with other therapeutic agent(s), each of the compounds of the combination can be administered simultaneously or sequentially and in any order, in jointly therapeutically effective amounts.

The 1-(β-D-glucopyranosyl)-3-(phenylthienylmethyl) benzene derivative of formula (A) can be prepared, for example, by a process as described in WO 2005/012326. And compound (A) hemihydrate can be prepared by a process described in WO 2008/069327. Compound (A) may be referred to as 1-(β-D-glucopyranosyl)-4-methyl-3-[5-(4-fluorophenyl)-2-thienylmethyl]benzene or (1S)-1,5-anhydro-1-(3-{[5-(4-fluorophenyl)-2-thienyl]methyl}-4-methylphenyl)-D-glucitol, depending on the nomenclature.

In another example, 1-β-D-glucopyranosyl-substituted phenylthienylmethyl benzene derivative of formula (A) can be prepared in a process comprising the steps of:
(a) coupling a compound of formula (V) with a compound of formula (VI) and treating the resulting compound with methanesulfonic acid:

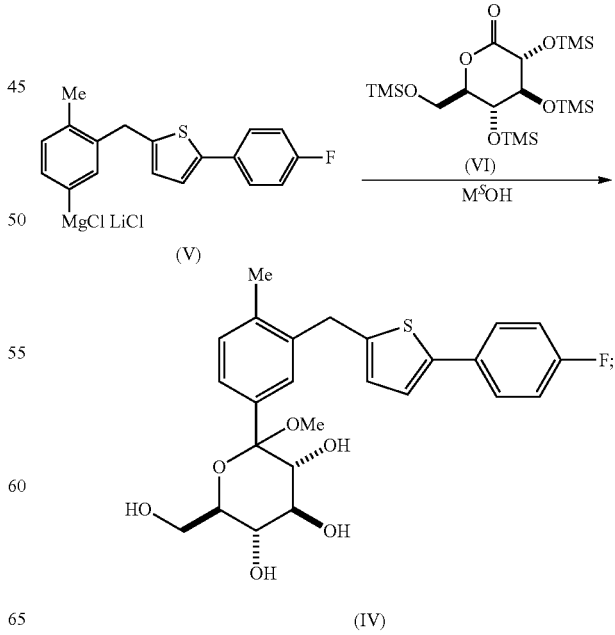

(b) acetylating the compound of formula (IV):

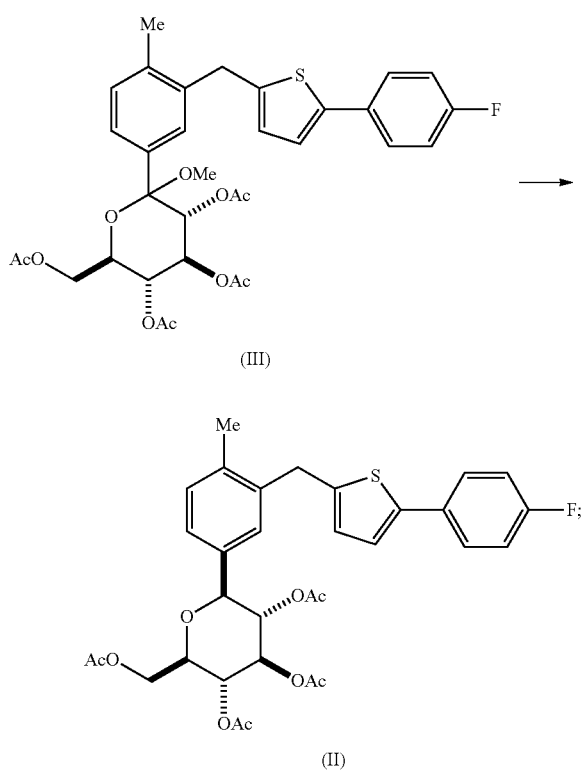

(d) reducing the compound of formula (III):

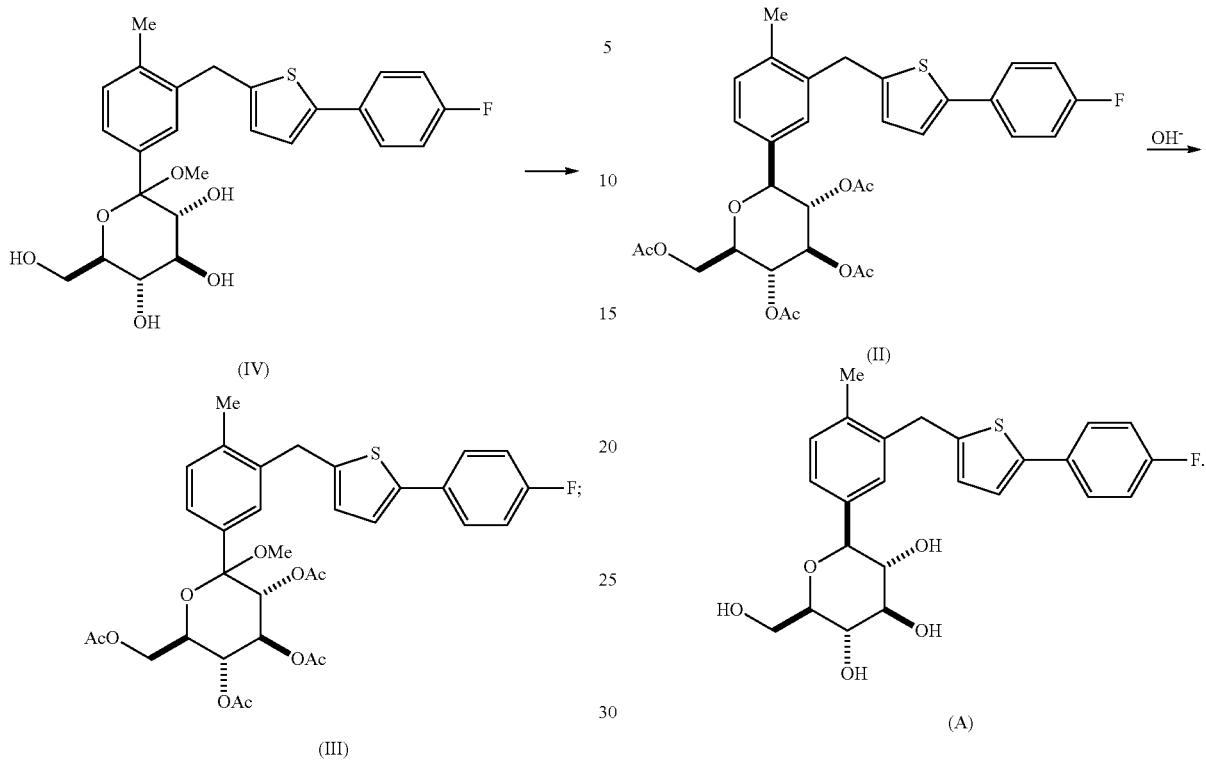

and, (e) hydrolyzing the compound of formula (II):

The coupling reaction is typically carried out in tetrahydrofuran at lower or ambient temperature. The resulting compound is typically treated with methanesulfonic acid in methanol to give the compound of formula (IV).

The acetylation can be carried out with acetyl anhydride in a suitable solvent such as toluene and ethyl acetate in the presence of a base such as N-methylmorpholine and 4-dimethylaminopyridine at lower or ambient temperature.

The reduction is typically carried out by treating the compound of formula (III) with a reducing agent, such as triethylsilyl hydride and a Lewis acid, such as $BF_3 \cdot Et_2O$, in a suitable solvent such as $CH_3CN$, and water.

The hydrolysis is typically carried out by treating the compound of formula (II) with a base such as lithium hydroxide in a suitable solvent such as methanol, tetrahydrofuran and water.

Compound (A) is typically treated with water-containing solvent to form a crystal slurry of a hemihydrate thereof and separating out a hemihydrate thereof.

The activity of compound (A) or a pharmaceutically acceptable salt thereof can be determined using, for example, the assay system described in US 2005/0233988 A1 or any appropriate assay system known in the art.

The following examples are provided to describe the invention in further detail. These examples are intended to illustrate and not to limit the invention.

EXAMPLES

Example 1

Table 1 shows the components and compositions of the tablets. The tablets were prepared in accordance with the method described below.

TABLE 1

Composition of Drug Product

| Component | Function | mg/tablet | % w/w | Quantity/Batch (g) |
|---|---|---|---|---|
| <Intra-granular Additions> | | | | |
| Compound (A) | Drug Substance | 204.0* | 71.33 | 4080 |
| D-Mannitol | Filler | 36.0 | 12.59 | 720 |
| Hydroxypropyl Cellulose | Binder | 8.0 | 2.80 | 160 |
| Purified Water | Processing Agent | ** | ** | ** |
| <Extra-granular Additions> | | | | |
| Croscarmellose Sodium | Disintegrant | 11.2 | 3.92 | 224 |
| Talc | Lubricant | 2.8 | 0.98 | 56 |
| Sodium Stearyl Fumarate | Lubricant | 8.0 | 2.80 | 160 |
| Core Totals | | 270.0 | 94.4 | 5400 |
| Opadry □II*** | Coating Agent | 16.0 | 5.59 | 320 |
| Purified Water | Processing Agent | ** | ** | ** |
| Totals | | 286.0 | 100.0 | 5720 |

*Amount of hemihydrate, equivalent to 200 mg anhydrous form of drug substance
** Purified water is used during granulation and coating process but removed during the drying process
***15% solid content suspension Compound (A), D-mannitol and hydroxypropyl cellulose were blended in High Shear Mixer (High Speed Mixer; FS-GS-25J, Fukae Powtex Co., Osaka, Japan) for one minute. The mix was granulated adding purified water. After the completion of adding water, the granulation was continued for two minutes.

The wet granules were set in fluidized bed drier (Flow Coater; FLO-5M, Freund Co., Tokyo, Japan) and dried. During the drying, the samples of granules were taken from the fluidized bed drier at certain intervals. The moisture level during drying was determined to measure the loss on drying (LOD) of the sample.

The dried granules were sized with a 22 mesh (710 μm) sieve. The granules of oversized fraction were crushed by using New Speed Mill (ND-10S, Okada Seiko Co. Ltd., Tokyo, Japan) with 2.5 mm and 1.0 mm circular holes screen, followed by passing through a 22 mesh sieve completely.

Extra-granular Additions (croscarmellose sodium, talc and sodium stearyl fumarate) were premixed with a portion of sized granules in a plastic bag and passed through a 22 mesh (710 μm) sieve respectively. These premixed powders and the residual sized granules were blended for 4 minutes in a V type Blender (SVM-50, Meiwa Kougyo Co., Nagoya, Japan).

The final blend was compressed into tablets using a rotary press (VIRGO0518SS2AZ, Kikusui Seisakusyo Ltd., Kyoto, Japan) equipped with round biconvex punches of 9 mm in diameter. Tablets were compressed at varying compression forces from 4.2 KN to 6.5 KN. The coefficient of variation in tablet weight was less than 1.0% and the friability of tablet was less than 0.2%. Tablet hardness was increased from 67 N to 99 N and the corresponding tablet thickness was decreased from 4.54 mm to 4.35 mm. These results show the good compressibility and compactibility of the final blend. Additionally, In vitro drug release was measured using the Japanese Pharmacopoeia XV(JP XV) apparatus II fitted with paddles rotated at 75 rpm. Dissolution medium was used phosphate buffer pH 6.8 (2nd fluid in JP XV) containing 0.1% w/w polysorbate 80. A dissolved amount of Compound (A) was between about 90% and 94% at 30 minutes. The dissolution rate was not affected by compression force.

The compressed tablets were coated in aqueous film coating system using Opadry II 15% solid content suspension based on polyvinyl alcohol. Tablet coating was carried out in a conventional coating pan (Doria coater, DRC-500, Powrex Co., Hyougo, Japan) using spray coating technique and conducted under a generalized manufacturing condition. The tablets were coated without any problem and the prepared tablets were free from defects such as picking and peeling.

Example 2

Tablets containing 102 mg of compound (A) hemihydrate (which corresponds to 100 mg of compound (A)) were prepared in accordance with the method described in Example 1. Components and compositions of the tablets are described in Table 2.

TABLE 2

Composition of Tablet

| Component | mg/tablet |
|---|---|
| Compound (A) | 102.0* |
| D-Mannitol | 18.0 |
| Hydroxypropyl Cellulose | 4.0 |
| Croscarmellose Sodium | 5.6 |
| Talc | 1.4 |
| Sodium Stearyl Fumarate | 4.0 |
| Opadry II | 10.0 |

*Amount of hemihydrate, equivalent to 100 mg of anhydrous compound (A)

Example 3

Tablets containing 51 mg of compound (A) hemihydrate were prepared in accordance with the method described in Example 1. Components and compositions of the tablet are described in Table 3.

TABLE 3

Composition of Tablet

| Component | mg/tablet |
|---|---|
| Compound (A) | 51.0* |
| D-Mannitol | 9.0 |
| Hydroxypropyl Cellulose | 2.0 |
| Croscarmellose Sodium | 2.8 |
| Talc | 0.7 |
| Sodium Stearyl Fumarate | 2.0 |
| Opadry II | 5.5 |

*Amount of hemihydrate, equivalent to 50 mg of anhydrous compound (A)

Example 4

Tablets containing 306 mg of compound (A) hemihydrate (which corresponds to 300 mg of compound (A)) were prepared in accordance with the method described below. Components and compositions of the tablets are described in Table 4.

TABLE 4

Composition of Tablet

| Component | mg/tablet |
| --- | --- |
| Compound (A) | 306.0* |
| D-Mannitol | 54.0 |
| Hydroxypropyl Cellulose | 12.0 |
| Croscarmellose Sodium | 16.8 |
| Talc | 4.2 |
| Sodium Stearyl Fumarate | 12.0 |

*Amount of hemihydrate, equivalent to 300 mg of anhydrous compound (A)

Compound (A), D-mannitol and hydroxypropyl cellulose were blended in High Shear Mixer (Virtical Granulator; VG-100, Powrex Co., Hyogo, Japan) for one minute. The mix was granulated adding purified water. After the completion of adding water, the granulation was continued for two minutes.

The wet granules were crushed by using New Speed Mill (ND-10S, Okada Seiko Co. Ltd., Tokyo, Japan) with 5.0 mm circular holes screen, and were set in fluidized bed drier (Flow Coater; NFLO-30SJ, Freund Co., Tokyo, Japan) and dried.

The dried granules were sized with a 22 mesh (710 μm) sieve. The granules of oversized fraction were crushed by using New Speed Mill (ND-10S, Okada Seiko Co. Ltd., Tokyo, Japan) with 5.0 mm, 2.5 mm and 1.0 mm circular holes screen, followed by passing through a 22 mesh sieve completely.

The sized granules were set in fluidized bed drier (Flow Coater; NFLO-30SJ, Freund Co., Tokyo, Japan) and dried once again.

During the drying, the samples of granules were taken from the fluidized bed drier at certain intervals. The moisture level during drying was determined to measure the loss on drying (LOD) of the sample.

Extra-granular additions (croscarmellose sodium, talc and sodium stearyl fumarate) were premixed with a portion of sized granules in a plastic bag and passed through a 22 mesh (710 μm) sieve respectively. These premixed powders and the residual sized granules were blended for 4 minutes in a W type Blender (W-60, Tokujyu Kousakusyo Co., Kanagawa, Japan).

The final blend was compressed into tablets using a single punch press (Compaction Analyzer, Kikusui Seisakusyo Ltd., Kyoto, Japan) equipped with oval shaped punch (major axis:13.5 mm, minor axis:7.70 mm). Tablets were compressed at varying compression forces from 4.2 KN to 5.4 KN. Tablet hardness was increased from 99 N to 121 N and the corresponding tablet thickness was decreased from 5.12 mm to 5.00 mm. These results show the good compressibility and compactibility of the final blend. Additionally, In vitro drug release was measured using the Japanese Pharmacopoeia XV(JP XV) apparatus II fitted with paddles rotated at 50 rpm. Dissolution medium was used phosphate buffer pH 6.8 (2nd fluid in JP XV) containing 0.1% w/w polysorbate 80. A dissolved amount of Compound A was between about 77% and 82% at 60 minutes. The dissolution rate was not affected by compression force.

Experiments (1) Methods

Tablets were prepared in accordance with the method described below, where the components and compositions of the tablets are described in Table 5.

Compound (A), D-mannitol and hydroxypropyl cellulose were blended in High Shear Mixer (High Speed Mixer; LFS-GS-1, Fukae Powtex Co., Osaka, Japan). The mix was granulated adding purified water. After the completion of adding water, the granulation was continued.

The wet granules were set in fluidized bed drier (Multiplex; MP-01/03, Powrex Co., Hyougo, Japan) and dried until the product temperature reaches 40° C.

The dried granules were sized with a 22 mesh (710 μm) sieve. The granules of oversized fraction were crushed by using Power Mill (P-02S, Dalton Co. Ltd., Tokyo, Japan) with 2 mm herringbone screen and 1.0 mm circular holes screen, followed by passing through a 22 mesh sieve completely.

Extra-granular additions (croscarmellose sodium, magnesium stearate, talc and sodium stearyl fumarate) were passed through a 42 mesh (355 μm) sieve. These powders and sized granules were put in a plastic bag and mixed 50 times Mixed granules were compressed into tablets using a rotary press (Collect 12HUK, Kikusui Seisakusyo Ltd., Kyoto, Japan) equipped with round biconvex punches of 9 mm in diameter. Tablets were compressed at varying compression forces from 0.3 ton to 1.5 ton, and tablet thickness, tablet hardness and ejection force during tableting were measured.

TABLE 5

| | mg/Tablet | | |
| --- | --- | --- | --- |
| Component | Experiment 1 (Ex 1) | Experiment 2 (Ex 2) | Experiment 3 (Ex 3) |
| Compound (A) | 200.0 | 200.0 | 200.0 |
| D-mannitol | 44.7 | 44.7 | 40.0 |
| Hydroxypropyl Methylcellulose | 11.4 | — | — |
| Hydroxypropyl Cellulose | — | 11.4 | 8.1 |
| Croscarmellose Sodium | 11.2 | 11.2 | 11.2 |
| Magnesium Stearate | 2.7 | — | — |
| Sodium Stearyl Fumarate | — | 2.7 | 2.7 |
| Talc | — | — | 8.0 |
| Totals | 270.0 | 270.0 | 270.0 |

(2) Results

The results of the ejection force during tableting and the resultant tablet characteristics of thickness and hardness are shown in the following tables.

Ex 1

| | Compression force (ton) | | | |
| --- | --- | --- | --- | --- |
| | 0.5 | 0.7 | 0.9 | 1.1 |
| thickness (mm) | 4.25 | 4.12 | 4.09 | 4.07 |
| hardness (N) | 84 | 109 | 117 | 119 |

Ex 2

| | Compression force (ton) | | | |
|---|---|---|---|---|
| | 0.4 | 0.8 | 1.1 | 1.5 |
| Thickness (mm) | 4.37 | 4.14 | 4.07 | 4.00 |
| Hardness (N) | 77 | 137 | 156 | 174 |
| Ejection force (kg) | 15 | 20 | 21 | 22 |

Ex 3

| | Compression force (ton) | | | | |
|---|---|---|---|---|---|
| | 0.3 | 0.5 | 0.7 | 0.9 | 1.1 |
| Thickness (mm) | 4.54 | 4.30 | 4.15 | 4.08 | 4.03 |
| Hardness (N) | 51 | 89 | 120 | 141 | 160 |
| Ejection force (kg) | 4 | 7 | 10 | 11 | 12 |

Reference Example (1) 2-(5-Iodo-2-methylbenzyl)-5-(4-fluorophenyl)thiophene

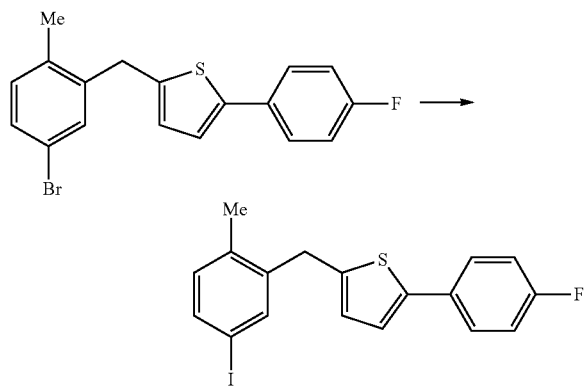

2-(5-Bromo-2-methylbenzyl)-5-(4-fluorophenyl)thiophene (100 g; see WO 2005/012326 pamphlet) was dissolved in toluene (300 mL) at room temperature under N₂ atmosphere. Sodium iodide (83 g), copper (I) iodide (2.64 g), N,N'-dimethyl ethylenediamine (2.94 mL) and diglyme (50 mL) was added to the mixture at room temperature. The reaction mixture was heated to reflux temperature and stirred for 36 hours. Ethyl acetate (300 mL) was added to the mixture at 40° C. and the mixture was filtered using activated carbon pre-coated filter. The filtrate was washed and then evaporated. The resulting residue was suspended in methanol (426 mL) at reflux temperature for 75 minutes. The resulting slurry was cooled to 25° C. and stirred for 1 hour. The precipitate was filtered and washed with methanol, then dried at 50° C. in vacuo to give 2-(5-iodo-2-methylbenzyl)-5-(4-fluorophenyl)thiophene (94.9 g) as white crystals. m/z (APCI), 409 (M$^+$+H); mp 109-110° C.

(2) Methyl 1-C-(3-{[5-(4-fluorophenyl)-2-thienyl]methyl}-4-methyl-phenyl)-D-glucopyranoside

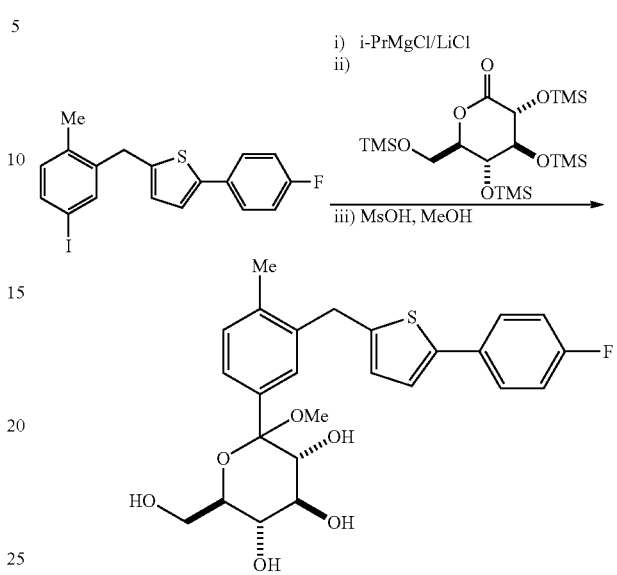

To a solution of 2-(5-iodo-2-methylbenzyl)-5-(4-fluorophenyl)thiophene (40.0 g) in anhydrous THF (200 mL) was added a solution of i-propyl magnesium chloride/lithium chloride in THF (14.5 wt %, 76.4 g) dropwise under N₂ at 0-5° C. The mixture was stirred for 1 hour at the same temperature, and then the mixture was added dropwise to a solution of 2,3,4,6-tetrakis-O-(trimethylsilyl)-D-glucopyrano-1,5-lactone (54.9 g; see U.S. Pat. No. 6,515,117) in anhydrous THF (80 mL) at 0-5° C. The reaction mixture was stirred for 2 hours and quenched with a solution of methanesulfonic acid (11.3 g) in methanol (400 mL) under cooling. Upon complete addition, the mixture was stirred for 2 hours under cooling, and then was warmed to room temperature and stirred for 4 hours. The mixture was quenched in a solution of NaHCO₃ (4.12 g) in H₂O (400 mL) under cooling. The mixture was allowed to warm to room temperature, and then n-heptane was added to the mixture. After phase separation, the aqueous phase was extracted with ethyl acetate and toluene. The combined organic layer was washed with 5% aqueous NaHCO₃ solution, dried over anhydrous MgSO₄, and filtered to afford a solution of methyl 1-C-(3-{[5-(4-fluorophenyl)-2-thienyl]methyl}-4-methylphenyl)-D-glucopyranoside in ethyl acetate and toluene. m/z (APCI), 443 (M$^+$-MeOH).

(3) Methyl 2,3,4,6-tetra-O-acetyl-1-C-(3-{[5-(4-fluorophenyl)-2-thienyl]methyl}-4-methylphenyl)-D-glucopyranoside

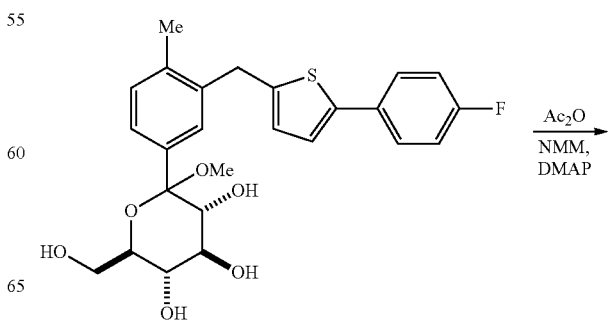

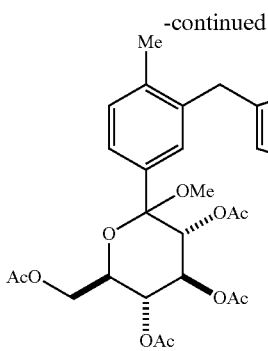

To a stirred solution of methyl 1-C-(3-{[5-(4-fluorophenyl)-2-thienyl]methyl}-4-methylphenyl)-D-glucopyranoside (net weight 10.54 g) in toluene and ethyl acetate was added N-methylmorpholine (11.9 g) and 4-dimethylaminopyridine (217 mg) at room temperature. The solution was cooled to 0° C. and acetic anhydride (52.7 mL) was added dropwise below 15° C. The reaction mixture was allowed to warm to room temperature and stirred for 15 hours. The mixture was quenched with 28% $NH_3$ aqueous solution (ca. 31.6 mL) while maintaining pH range of 6 to 7. Water was added to the mixture and separated. The organic layer was washed with water and brine, dried over anhydrous $MgSO_4$ and filtered. The filtrate was concentrated in vacuo to give (17.59 g) as yellow oil. m/z (APCI) 660 ($M^+$+$NH_4$).

(4) (1 S)-2,3,4,6-Tetra-O-acetyl-1,5-anhydro-1-(3-{[5-(4-fluorophenyl)-2-thienyl]methyl}-4-methyl-phenyl)-D-glucitol

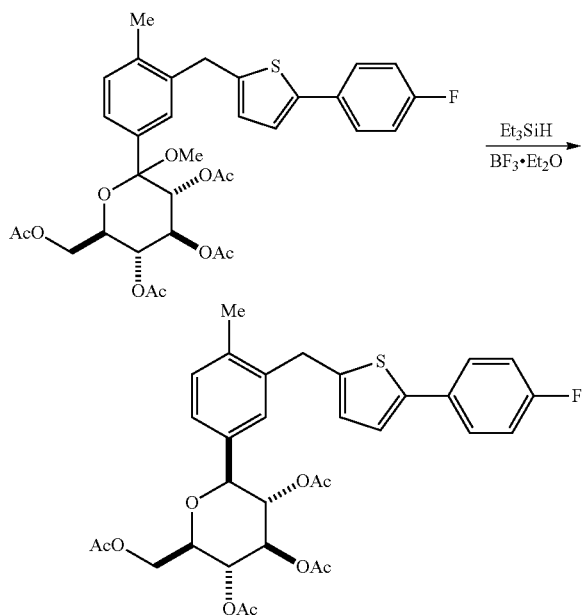

To a stirred solution of the above compound (net weight 14.25 g) in acetonitrile (114 mL) was added triethylsilane (7.74 g) at room temperature. The solution was cooled to 0° C. and boron trifluoride etherate (9.45 g) was added dropwise for 10 minutes. The reaction mixture was stirred at 0° C. for 4 hours. The mixture was quenched in a solution of 10% $K_2CO_3$ aqueous solution (156.8 mL) under cooling. The mixture was allowed to warm to room temperature and stirred for 15 minutes. After separation, water and ethyl acetate was added to the organic layer. The organic layer was washed with brine, and filtered. The filtrate was concentrated in vacuo. The resulting residue was suspended in ethanol and evaporated (twice). Ethanol was added to the residue and the resulting mixture was stirred for 30 minutes at 50° C., then cooled on an ice-bath. The precipitate was filtered and washed twice with ethanol, then dried to give (1S)-2,3,4,6-tetra-O-acetyl-1,5-anhydro-1-(3-{[5-(4-fluorophenyl)-2-thienyl]methyl}-4-methylphenyl)-D-glucitol (11.12 g) as white crystals. m/z (APCI) 630 ($M^+$+$NH_4$); mp. 160-170° C.

(5) (1S)-1,5-Anhydro-1-(3-{[5-(4-fluorophenyl)-2-thienyl]methyl}-4-methyl-phenyl)-D-glucitol

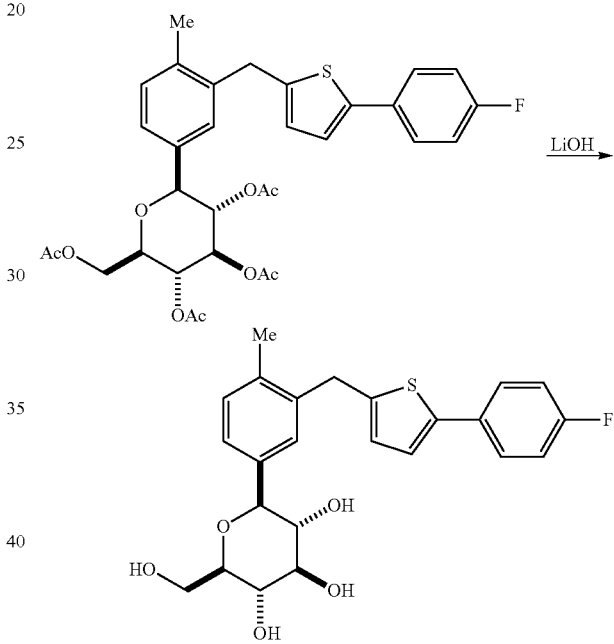

(1 S)-2,3,4,6-Tetra-O-acetyl-1,5-anhydro-1-(3-{[5-(4-fluorophenyl)-2-thienyl]methyl}-4-methylphenyl)-D-glucitol (5 g) was dissolved in methanol (35 mL) and tetrahydrofuran (25 mL) at room temperature. A solution of LiOH hydrate (192 mg) in water (10 mL) was added dropwise to the mixture for 30 minutes at 20-24° C. After the mixture was stirred for 19 hours at room temperature, the solvent was evaporated in vacuo. The residue was partitioned to ethyl acetate (50 mL) and water (25 mL), stirred for 15 minutes, then the layers were separated. The organic layer was washed with water. The organic layer was dried over $Na_2SO_4$, filtered using activated carbon pre-coated filter and evaporated. The resulting residue was dissolved in ethyl acetate (11.1 mL) at 40° C., water (241 mL) was added to the mixture at the same temperature. n-Heptane (5.6 mL) was added to the mixture at ° C., then the mixture was seeded with a slight amount of (1S)-1,5-anhydro-1-(3-{[5-(4-fluorophenyl)-2-thienyl]methyl}-4-methylphenyl)-D-glucitol at same temperature. After stirred for 1 hour at 35° C., n-heptane (2.6 mL) was added slowly to the mixture. The resulting mixture was cooled. The precipitate was filtered and washed with ethyl acetate/n-heptane, then dried to give hemihydrate of (1S)-1,5-anhydro-1-(3-{[5-(4-fluorophenyl)-2-thienyl]methyl}-4-methyl-phenyl)-D-glucitol (2.93 g) as white crystals. m/z (APCI) 462 (M$^+$+NH$_4$); mp. 106-107° C.

The invention claimed is:

1. A tablet comprising a compound of formula (A):

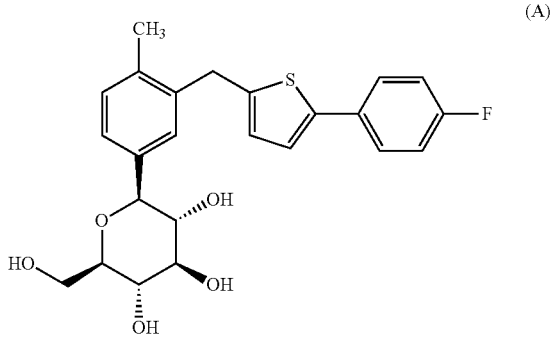 [SMILES: Cc1ccc([C@@H]2O[C@H](CO)[C@@H](O)[C@H](O)[C@H]2O)cc1Cc1ccc(-c2ccc(F)cc2)s1]

(A)

or a pharmaceutically acceptable salt thereof, a lubricant, and one or more pharmaceutically acceptable additives, wherein compound (A) or a pharmaceutically acceptable salt thereof is present in an amount within the range of from about 65 to 90% by weight of tablet, and wherein the lubricant is talc and sodium stearyl fumarate and is present in an amount of from about 1 to 10% by weight of the tablet.

2. The tablet according to claim 1, wherein a pharmaceutically acceptable salt of compound (A) is hemihydrate of compound (A).

3. The tablet according to claim 1, wherein the pharmaceutically acceptable additives comprise a bulking agent (a filler), a binder, and a disintegrant.

4. The tablet of claim 3, wherein a) compound (A) or a pharmaceutically acceptable salt thereof is present in an amount within the range of from 65 to 90% by weight of tablet; b) the bulking agent (the filler) is present in an amount within the range of from about 0 to 70% by weight of tablet; c) the binder is present in an amount within the range of from about 1 to 25% by weight of tablet; d) the disintegrant is present in an amount within the range of from about 1 to 25% by weight of tablet; and e) the lubricant is present in an amount within the range of from about 1 to 10% by weight of tablet.

5. The tablet of claim 3, wherein a) compound (A) or a pharmaceutically acceptable salt thereof is present in an amount within the range of from 65 to 90% by weight of tablet; b) the bulking agent or filler is present in an amount within the range of from about 5 to 15% by weight of tablet; c) the binder is present in an amount within the range of from about 1 to 5% by weight of tablet; d) the disintegrant is present in an amount within the range of from about 1 to 5% by weight of tablet; and e) the lubricant is present in an amount within the range of from about 1 to 10% by weight of tablet.

6. The tablet of claim 3, wherein compound (A) or a pharmaceutically acceptable salt thereof is present in an amount of 70±2% by weight of tablet; the bulking agent or filler is present in an amount of 12±2% by weight of tablet; the binder is present in an amount of 3±1% by weight of tablet; the disintegrant is present in an amount of 4±1% by weight of tablet; and the lubricant is present in an amount of 4±2% by weight of tablet.

7. The tablet of claim 5, which further comprises a coating agent in an amount within the range of from 3 to 10% by weight of tablet.

8. The tablet according to claim 1, wherein a) compound (A) hemihydrate is present in an amount of about 204 mg; b) D-mannitol is present in an amount of about 36 mg; c) hydroxypropyl cellulose is present in an amount of about 8 mg; d) croscarmellose sodium is present in an amount of about 11.2 mg; e) talc is present in an amount of about 2.8 mg; and f) sodium stearyl fumarate is present in an amount of about 8 mg.

9. The tablet according to claim 1, wherein a) compound (A) hemihydrate is present in an amount of about 102 mg; b) D-mannitol is present in an amount of about 18 mg; c) hydroxypropyl cellulose is present in an amount of about 4 mg; d) croscarmellose sodium is present in an amount of about 5.6 mg; e) talc is present in an amount of about 1.4 mg; and f) sodium stearyl fumarate is present in an amount of about 4 mg.

10. A method for treatment or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, diabetic complications, atherosclerosis, or hypertension, which comprises administering to a mammalian species in need of treatment a therapeutically effective amount of the tablet as set forth in claim 1.

11. A method for treatment of type 1 or type 2 diabetes mellitus, which comprises administering to a mammalian species in need of treatment a therapeutically effective amount of the tablet as set forth in claim 1 alone, or in combination with another antidiabetic agent, an agent for treating diabetic complications, an anti-obesity agent, an anti-hypertensive agent, an anti-platelet agent, an anti-atherosclerotic agent and/or a hypolipidemic agent.

12. The tablet of claim 1 for treating or delaying the progression or onset of diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glycerol, hyperlipidemia, obesity, hypertriglyceridemia, Syndrome X, atherosclerosis, or hypertension.

13. The tablet according to claim 1, wherein the pharmaceutically acceptable additives comprise at least one selected from the group consisting of surfactants, flavors, colorants, and sweetenings.

* * * * *